(12) United States Patent
Yodfat et al.

(10) Patent No.: US 9,798,859 B2
(45) Date of Patent: Oct. 24, 2017

(54) FLUID DELIVERY DEVICE AND METHODS OF ITS OPERATION

(75) Inventors: Ofer Yodfat, Maccabim-Reut (IL); Ido Nir-Shafrir, Yoqneam Illit (IL)

(73) Assignee: ROCHE DIABETES CARE, INC, Indianapolis, IN (US)

( * ) Notice: Subject to any disclaimer, the term of this patent is extended or adjusted under 35 U.S.C. 154(b) by 651 days.

(21) Appl. No.: 11/989,677

(22) PCT Filed: Jul. 6, 2007

(86) PCT No.: PCT/US2007/015562
§ 371 (c)(1),
(2), (4) Date: Jan. 13, 2011

(65) Prior Publication Data
US 2011/0112696 A1    May 12, 2011

(51) Int. Cl.
| G05B 11/01 | (2006.01) |
| G06F 19/00 | (2011.01) |
| G05D 7/06 | (2006.01) |
| A61M 5/142 | (2006.01) |

(52) U.S. Cl.
CPC ....... G06F 19/3412 (2013.01); G05D 7/0676 (2013.01); G06F 19/3468 (2013.01); A61M 2005/14268 (2013.01)

(58) Field of Classification Search
USPC ................. 340/4.3, 4.31, 12.29, 12.3, 12.37; 604/890.1; 607/30, 31, 59, 60
See application file for complete search history.

(56) References Cited

U.S. PATENT DOCUMENTS

| 3,631,847 | A |   | 1/1972  | Hobbs, II |
| 3,771,694 | A |   | 11/1973 | Kaminski |
| 4,498,843 | A |   | 2/1985  | Schneider et al. |
| 4,544,369 | A |   | 10/1985 | Skakoon et al. |
| 4,657,486 | A |   | 4/1987  | Stempfle et al. |
| 4,715,786 | A |   | 12/1987 | Wolff et al. |
| 5,673,400 | A | * | 9/1997  | Kenny .......................... 710/306 |
| 5,957,895 | A |   | 9/1999  | Sage et al. |
| 6,073,113 | A | * | 6/2000  | Guinan ........................ 705/26.1 |
| 6,134,603 | A | * | 10/2000 | Jones et al. ................... 719/330 |
| 6,485,461 | B1 |  | 11/2002 | Mason et al. |
| 6,589,229 | B1 |  | 7/2003  | Connelly et al. |
| 6,629,154 | B1 | * | 9/2003 | Jones et al. ................... 719/330 |
| 6,723,072 | B2 |  | 4/2004  | Flaherty et al. |

(Continued)

FOREIGN PATENT DOCUMENTS

| EP | 1255383 A2 | 11/2002 |
| EP | 1 626 579 A1 | 2/2006 |

(Continued)

OTHER PUBLICATIONS

Written Opinion and International Search Report for PCT Application No. PCT/IB2007/004334.

(Continued)

Primary Examiner — Travis Hunnings
(74) Attorney, Agent, or Firm — Dinsmore & Shohl LLP

(57) ABSTRACT

A medicinal fluid delivery device and methods for its use are provided. The device can include a command means and a dispensing unit that can include a reusable part and a disposable, reservoir part. Software can be included that facilitates pairing and communications between a command means and the dispensing unit.

19 Claims, 14 Drawing Sheets

(56) References Cited

U.S. PATENT DOCUMENTS

| | | | |
|---|---|---|---|
| 6,738,670 B1 | 5/2004 | Almendinger et al. | |
| 6,740,059 B2 | 5/2004 | Flaherty | |
| 7,191,236 B2* | 3/2007 | Simpson-Young et al. | 709/228 |
| 7,383,541 B1* | 6/2008 | Banks et al. | 717/131 |
| 7,478,008 B2* | 1/2009 | Balss et al. | 702/137 |
| 7,636,549 B2* | 12/2009 | Ma et al. | 455/41.2 |
| 7,639,155 B2* | 12/2009 | Gauthier et al. | 340/4.3 |
| 7,769,605 B2* | 8/2010 | Brown | 705/3 |
| 7,797,331 B2* | 9/2010 | Theimer et al. | 707/769 |
| 8,315,708 B2* | 11/2012 | Berthelsdorf et al. | 607/60 |
| 2001/0041920 A1 | 11/2001 | Starkweather et al. | |
| 2003/0003892 A1* | 1/2003 | Makinen | 455/345 |
| 2003/0215210 A1* | 11/2003 | Yamazaki | 386/40 |
| 2004/0073795 A1 | 4/2004 | Jablon | |
| 2004/0078231 A1 | 4/2004 | Wilkes et al. | |
| 2004/0218613 A1* | 11/2004 | Fortman | 370/401 |
| 2004/0235446 A1 | 11/2004 | Flaherty et al. | |
| 2005/0063541 A1* | 3/2005 | Candelore | 380/239 |
| 2005/0240555 A1* | 10/2005 | Wilde et al. | 707/1 |
| 2005/0253682 A1* | 11/2005 | Kato et al. | 340/3.7 |
| 2005/0288738 A1 | 12/2005 | Bange et al. | |
| 2006/0003785 A1* | 1/2006 | Zatezalo | 455/519 |
| 2006/0006991 A1 | 1/2006 | Tyndall et al. | |
| 2006/0126832 A1* | 6/2006 | Takahashi | 380/30 |
| 2006/0198519 A9* | 9/2006 | Candelore | 380/239 |
| 2006/0217990 A1* | 9/2006 | Theimer et al. | 705/1 |
| 2006/0251256 A1* | 11/2006 | Asokan et al. | 380/270 |
| 2006/0262806 A1* | 11/2006 | Bouazizi | 370/448 |
| 2006/0271833 A1* | 11/2006 | Teranishi et al. | 714/799 |
| 2007/0080823 A1* | 4/2007 | Fu et al. | 340/825.22 |
| 2007/0106218 A1 | 5/2007 | Yodfat et al. | |
| 2007/0183600 A1* | 8/2007 | Smart | 380/286 |
| 2007/0220369 A1* | 9/2007 | Fayad et al. | 714/48 |
| 2007/0249286 A1* | 10/2007 | Ma et al. | 455/41.3 |
| 2008/0004601 A1* | 1/2008 | Jennewine et al. | 604/890.1 |
| 2008/0057890 A1* | 3/2008 | McKillop et al. | 455/185.1 |
| 2008/0058900 A1* | 3/2008 | Berthelsdorf et al. | 607/59 |
| 2008/0070501 A1* | 3/2008 | Wyld | 455/41.2 |
| 2008/0189794 A1* | 8/2008 | Staring et al. | 726/27 |
| 2008/0215035 A1 | 9/2008 | Yodfat et al. | |
| 2008/0228428 A1* | 9/2008 | Balss et al. | 702/137 |
| 2008/0287062 A1* | 11/2008 | Claus et al. | 455/41.2 |
| 2008/0320190 A1* | 12/2008 | Lydon et al. | 710/106 |
| 2009/0006133 A1* | 1/2009 | Weinert et al. | 705/3 |
| 2009/0009391 A1* | 1/2009 | Fox et al. | 342/372 |
| 2009/0156123 A1* | 6/2009 | Kim | 455/41.2 |
| 2009/0164134 A1* | 6/2009 | Drucker et al. | 702/19 |
| 2010/0217230 A1 | 8/2010 | Yodfat et al. | |
| 2010/0218044 A1* | 8/2010 | Roblett et al. | 714/32 |
| 2011/0022191 A1* | 1/2011 | Amit et al. | 700/21 |
| 2011/0066297 A1* | 3/2011 | Saberi et al. | 700/287 |

FOREIGN PATENT DOCUMENTS

| | | |
|---|---|---|
| EP | 1626579 A1 | 2/2006 |
| WO | 2004079962 A2 | 9/2004 |
| WO | WO-2007052277 A1 | 5/2007 |
| WO | 2010055504 A1 | 5/2010 |

OTHER PUBLICATIONS

International Search Report, PCT Application No. PCT/IB2007/004334 dated Oct. 30, 2008.
Summons to Attend Oral Proceedings Pursuant to Rule 115(1) EPC pertaining to EP07866615.3 dated May 8, 2017.

* cited by examiner

FLUID DELIVERY DEVICE AND METHODS OF ITS OPERATION

CROSS REFERENCE TO RELATED APPLICATIONS

This application is a national stage entry of PCT/IB2007/004334 (PCT/US07/15562), having an international filing date of Jul. 6, 2007, which claims priority to U.S. provisional patent application Nos. 60/819,336, filed Jul. 7, 2006 and 60/819,356, filed Jul. 8, 2006. Each of the foregoing disclosures is expressly incorporated herein in its entirety.

RELATED APPLICATIONS

This application claims the priority of U.S. Provisional Application Ser. Nos. 60/819,336, filed Jul. 7, 2006 and entitled "System and Methods of Operation of a Medicinal Fluid Delivery System," and 60/819,356, filed Jul. 8, 2006 and entitled "Systems and Methods of Communications of a Medicinal Fluid Delivery System," the disclosures of which are hereby incorporated by reference in their entireties.

BACKGROUND

Medical treatment of various illnesses and medical conditions can include continuous drug infusion into various body compartments, such as subcutaneous and intra-venous injections. Diabetes mellitus patients, for example, are generally treated by administration of varying amounts of insulin throughout the day to control their blood glucose levels. In recent years, ambulatory portable insulin infusion pumps have emerged as a superior alternative to multiple daily syringe injections of insulin. These pumps, which deliver insulin at a continuous basal rate as well as in bolus volumes, were developed to liberate patients from repeated self-administered injections and to allow them to maintain a near-normal daily routine. Both basal and bolus dose volumes are generally controlled precisely, according to individual prescription, since an overdose or under-dose of insulin or other medicinal fluids can be fatal.

Several ambulatory insulin infusion devices are currently available. These devices generally have two portions: a reusable portion that contains, a dispenser, a controller and electronics, and a disposable portion that contains a syringe-type reservoir, a needle assembly with a cannula and a penetrating member, and a fluid delivery tube. In use, a patient typically fills the reservoir with insulin, attaches the needle and the delivery tube to the exit port of the reservoir, and then inserts the reservoir into the pump housing. After purging air out of the reservoir, tube and needle, the patient inserts the needle assembly, that includes the penetrating member and cannula, at a selected location on the body and withdraws the penetrating member. To avoid irritation and infection, the subcutaneous cannula is usually replaced and discarded after a relatively short period of time, such as two to three days, together with the empty reservoir. Examples of first generation disposable syringe-type reservoir and tubes were disclosed in U.S. Pat. No. 3,631,847 to Hobbs, U.S. Pat. No. 3,771,694 to Kaminski, U.S. Pat. No. 4,657,486 to Stempfle, and U.S. Pat. No. 4,544,369 to Skakoon. The driving mechanism of these devices can be a screw thread driven plunger controlling the programmed movement of a syringe piston. Other dispensing mechanisms have been also discussed, including peristaltic positive displacement pumps, in U.S. Pat. No. 4,498,843 to Schneider and U.S. Pat. No. 4,715,786 to Wolff. These devices are generally fairly large and heavy due to the configuration and the relatively large size of the driving mechanism of the syringe and the piston. This relatively bulky device is generally carried in a patient's pocket or attached to the belt. Consequently, the fluid delivery tube is typically quite long, usually longer than 60 cm, in order to permit needle insertion at remote sites of the body. Such uncomfortable, bulky devices with a long tube are rejected by many diabetic insulin users, since they disturb regular activities, such as sleeping and swimming. Furthermore, the effect of the image projected on the teenagers'body is unacceptable. In addition, the delivery tube excludes some optional remote insertion sites, like buttocks, arms and legs.

Recently, remote controlled, skin adherable delivery devices have been introduced. Such a device generally includes a housing with a bottom surface adapted to contact a patient's skin, a reservoir disposed within the housing, and an injection needle adapted to communicate with the reservoir. These skin adherable devices also should be discarded on a relatively short duty cycle such as every two to three days for similar reasons to those discussed above for pump infusion sets. Such adherable devices have been disclosed in U.S. Pat. No. 5,957,895 to Sage, U.S. Pat. No. 6,589,229 to Connelly, and U.S. Pat. No. 6,740,059 to Flaherty. Additional configurations of skin adherable pumps have been disclosed in U.S. Pat. No. 6,723,072 to Flaherty and U.S. Pat. No. 6,485,461 to Mason. In general, these devices can be relatively bulky and expensive. Their high selling price is due to high production and accessory costs as well as the typical requirement that a user must discard the entire device, which typically includes relatively expensive components such as a driving mechanism and other electronics, every two to three days, including.

SUMMARY

The subject matter disclosed herein can be used in conjunction with a fluid delivery device that can include a dispensing unit and a commands means as discussed in greater detail below. Various communication methods that can be implemented by computer software or other logical instructions executed on one or both of the command means and the dispensing unit can enable pairing, communication, data recording, and other features for the command means and the dispensing unit. Among other possible advantages, substantial power savings may be realized for the dispensing unit. By initiating dispensing unit-command means communications from the dispensing unit instead of from the command means, the dispensing unit can reduce power consumption by components such as its wireless transceiver except during short periods when communications occur. This can be an important advantage in reducing the size of the dispensing unit as less space is needed for a larger battery or other power supply. A battery or other power supply for the dispensing unit can be included in a disposable part of a dispensing unit, which in some variations can be replaced only every few days. Size reductions in the dispensing unit can realize improvements in user comfort, ease of use of the dispensing unit, and manufacturing costs.

Additional advantages in reduction of manufacturing costs and reduction of dispensing unit size can also be realized due to the use of mirrored logbooks on the command means and the dispensing unit. Because the dispensing unit or at least a portion of the dispensing unit, such as for example a reusable part) can optionally be discardable on a relatively short time span, such as for example a few months, use of high capacity data storage components on the dispensing unit can increase costs and dimensions. The subject matter disclosed herein can allow use of a small capacity memory on the dispensing unit for storage of logbook data entries for a short period of time until these logbook data entries can be communicated to a command means that includes a larger capacity memory that stores a more complete version of the logbook, such as for example on a flash memory. Use of a larger capacity, more expensive memory on the command means is more cost effective because the command means can generally be more durable and therefore usable for a much longer period of time than the dispensing unit, such as for example a few years. Transfer of data packets from the small capacity dispensing unit logbook can occur as space in data packets sent from the dispensing unit is available. Data packets sent from the dispensing unit can be limited in size to minimize unnecessary, communication bandwidth. For example, a relatively long data logbook entry can be divided into various data packets which are shorter than the original data, and can be communicated in several communication cycles according to available space in communicated data packets. These approaches can provide communication efficiency advantages in addition to possible power saving, size reduction, and other advantages.

In a first aspect, a dispensing unit of a fluid delivery device can be paired with a command means. An unpaired status message is sent from the dispensing unit if the dispensing unit is not yet paired with a command means. After receiving an acceptance message from the command means, the dispensing unit checks the acceptance message to verify compatibility between the command means and the dispensing unit and then saves identification information for the command means on the dispensing unit if compatibility is verified.

The following optional features can be included in this aspect either individually or in combination. The dispensing unit can test for software faults on the dispensing unit before sending the unpaired status message. Compatibility of the selected unpaired remote control unit can be verified based on a protocol and/or software version of the selected unpaired remote control unit. The dispensing unit can wait for a next communication cycle to resend the unpaired status message if no acceptance message is received from the command means or if compatibility between the command means and the dispensing unit is not verified.

In a second interrelated aspect, a command means can be paired with a dispensing unit of a fluid delivery device by receiving a designation code entered at the command means by a user. The designation code can identify a specific dispensing unit. The command means can receive an unpaired status message from the dispensing unit and check the unpaired status message to verify compatibility between the command means and the dispensing unit. After sending an accept dispensing unit message, the command means can wait for an acknowledgment message from the dispensing unit and then save identification information for the specific dispensing unit on the command means if the acknowledgment message is received.

The following optional features can be included in this aspect either individually or in combination. The command means can receive a user command to begin a reusable part replacement sequence. A one-to-one communication link can be established between the command means and the specific dispensing unit. The command means can ignore messages received from other dispensing units to which the remote control unit is not paired. The command means can prompt the user to enter a second designation code for another specific dispensing unit if compatibility between the specific dispensing unit and the command means cannot be verified. The command means can end the if the unpaired status message is not received from the dispensing unit within a threshold time. The designation code can include a hash code or other truncated representation of a full identification code for the dispensing unit.

In a third interrelated aspect, communication between a dispensing unit of a fluid delivery device and a paired command means, can include sending a communication message from the dispensing unit at a beginning of a current communication cycle and then enabling, for a limited period of a time, a wireless receiver provided on the dispensing unit. The dispensing unit can handle an incoming message if the incoming message is received from the paired command means during the limited period of time. The dispensing unit can then wait for a next communication cycle to send a next communication message from the dispensing unit.

The following optional features can be included in this aspect either individually or in combination. Communication can be suspended from the dispensing unit if the incoming message received from the paired command means is a stop communication message or if no message is received from the paired command means for greater than a threshold number of communication cycles. A communication message from the dispensing unit can be sent on a next communication cycle after the current communication cycle ends.

In a fourth interrelated aspect, communication between a command means and a paired dispensing unit of a fluid delivery device can include receiving a communication initiation from a user at the command means and waiting for a status message from the paired dispensing unit. Status data from the paired dispensing unit can be handled by the command means if the status message is received from the paired dispensing unit. The command means can wait for a next status message from the paired dispensing unit if communication has not ended.

The following optional features can be included in this aspect either individually or in combination. Handling of status data can include retrieving new logbook entries included in the status message received from the dispensing unit. The command means can send one or more new messages to the paired dispensing unit or send a stop communication message and ending communication if no messages need to be sent. The command means can increment a count of failed communication cycles since a last successful receipt of an incoming message if no status message is received from the dispensing unit and end communication if the count exceeds a threshold.

In a fifth interrelated aspect, a fluid delivery logbook can be maintained on a dispensing unit of a fluid delivery device. At the start of a current communication cycle, the dispensing unit can generate a dispensing unit status message and add unacknowledged logbook entries to the dispensing unit status message if a logbook on the dispensing unit comprises entries that have not been acknowledged by a command means paired to the dispensing unit. The dispensing unit can send the dispensing unit status message also record receipt of the logbook entries sent in the dispensing unit status message by the command means if an acknowledgment message is received from the command means. The dispensing unit can wait until a next communication cycle before initiating further communication.

The following optional features can be included in this aspect either individually or in combination. The dispensing unit status message can report one or more of current operating status data for the dispensing unit, logbook data that have not yet been transferred to the commands means from the dispensing unit, and acknowledgment of receipt by the dispensing unit of previous messages sent from the command means.

In a sixth interrelated aspect, a fluid delivery logbook can be maintained on a command means of a fluid delivery device. A dispensing unit status message can be received at the command means from a dispensing unit paired to the command means. If new logbook entries are included in the dispensing unit status message, the new logbook entries can be added to the logbook on the command means. The command means can send an acknowledgment message to the dispensing unit.

In optional variations of the above aspects, the command means can comprise a remote control unit or a personal or laptop computer or handheld communication device. A fluid delivery device can optionally include a command means capable of executing software instructions that implement one or more of the above methods and a dispensing unit that includes a controller capable of executing software instructions implementing one or more of the above methods. A computer-readable or machine-readable medium can be provided that encodes instructions sufficient to cause a dispensing unit and/or a command means to implement one or more of the above methods.

DESCRIPTION OF THE DRAWINGS

This disclosure may be better understood upon reading the detailed description and by reference to the attached drawings, in which.

DETAILED DESCRIPTION

Next generation skin adherable dispensing patch units have been developed to address price issues and patient comfort and customization issues. Example of such devices are discussed in co-pending/co-owned U.S. patent application Ser. No. 11/397,115 and International Patent Application No. PCT/IL06/001276, the disclosures of which are incorporated herein by reference in their entireties. One such device is a dispensing unit having two parts: a reusable part that contains, driving and pumping mechanisms, electronics, and other relatively expensive components, and a disposable part that contains less expensive, discardable components such as a fluid reservoir, tubes, and batteries.

This concept provides the possibility for a cost-effective, skin adherable infusion device and allows diverse usage of the device, e.g. the use of various reservoir sizes, various needle and cannula types and implementation of versatile operational modes. This generation of infusion pumps allows for various applicable types of pumping mechanisms for the two-part device configuration. A preferred delivery mechanism is the peristaltic positive displacement pumping mechanism also discussed in co-pending/co-owned U.S. patent application Ser. No. 11/397,115 and International Patent Application No. PCT/IL06/001276. Alternative driving mechanisms, which can be applied in any one of the various pumping mechanisms, may include. DC motor, stepper motor, Shape Memory Alloy (SMA) actuator, etc.

This infusion device also includes electronics (typically a processor and associated other hardware) and software to provide controlled operation of the dispensing unit and to allow programming, commanding and data analysis. This may be carried out manually and/or automatically (and/or semi-automatically) by a patient, clinician, technician or any other user, via a remote control unit and/or manual input means located on the dispensing unit.

The presently disclosed subject matter provides, among other potential benefits, systems, methods, techniques, apparatus, and articles of manufacture pertaining to delivery of fluids to a patient's body via a fluid delivery device which comprises a dispensing unit 102 and a remote control unit 104. The dispensing unit 102 can employ a pumping mechanism (e.g. peristaltic, piston) and reservoir or other comparable fluid driving system. The remote control unit 104 can optionally be a single use device or alternatively be other command means like a multiple purpose computer or communication device such as for example a personal or laptop computer, a handheld communication device (cell phone, personal data assistant, handheld wireless device, or the like).

Figure 1A:
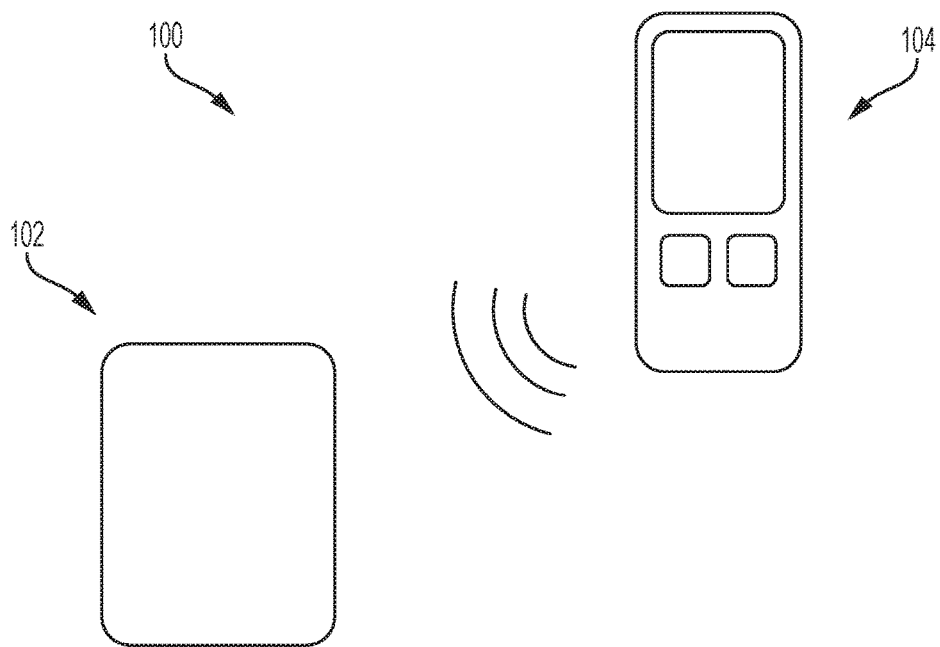
FIG. 1A, FIG. 1B, and FIG. 1C are box diagrams showing a fluid delivery device (1A), a single-part dispensing unit (1B), and a two-part dispensing unit (1C)
Figures 1B, 1C:
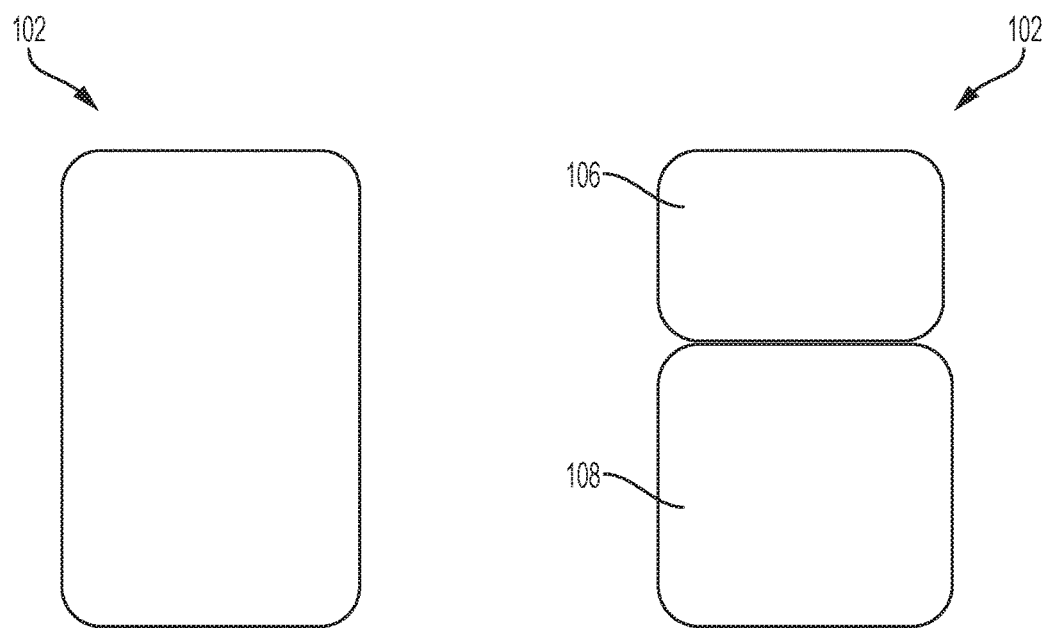

FIG. 1A shows an example of a medicinal fluid delivery system 100 that includes a dispensing unit 102 and a remote control unit 104. In one implementation shown in FIG. 1B, the dispensing unit 102 can be a single part. Alternatively, as shown in FIG. 1C, the dispensing unit 102 can include two parts: a reusable part 106 and a disposable part 108 that is detachably connectable to the reusable part 106. The dispensing unit 102 can employ different dispensing mechanisms, such as for example a syringe-type reservoir with a propelling plunger, peristaltic positive displacement pumps, and the like. In some variations, the dispensing unit 102 can be adhered to the patient's body. Such an adherable dispensing unit 102 can optionally be attached to the patient's body by direct adherence to the skin, using a well arrangement as disclosed in U.S. Provisional Patent Application No. 60/833, 110, or via a cradle unit as disclosed in U.S. Provisional Patent Application No. 60/876,679, or by other attachment techniques and/or methods.

Figure 2A:
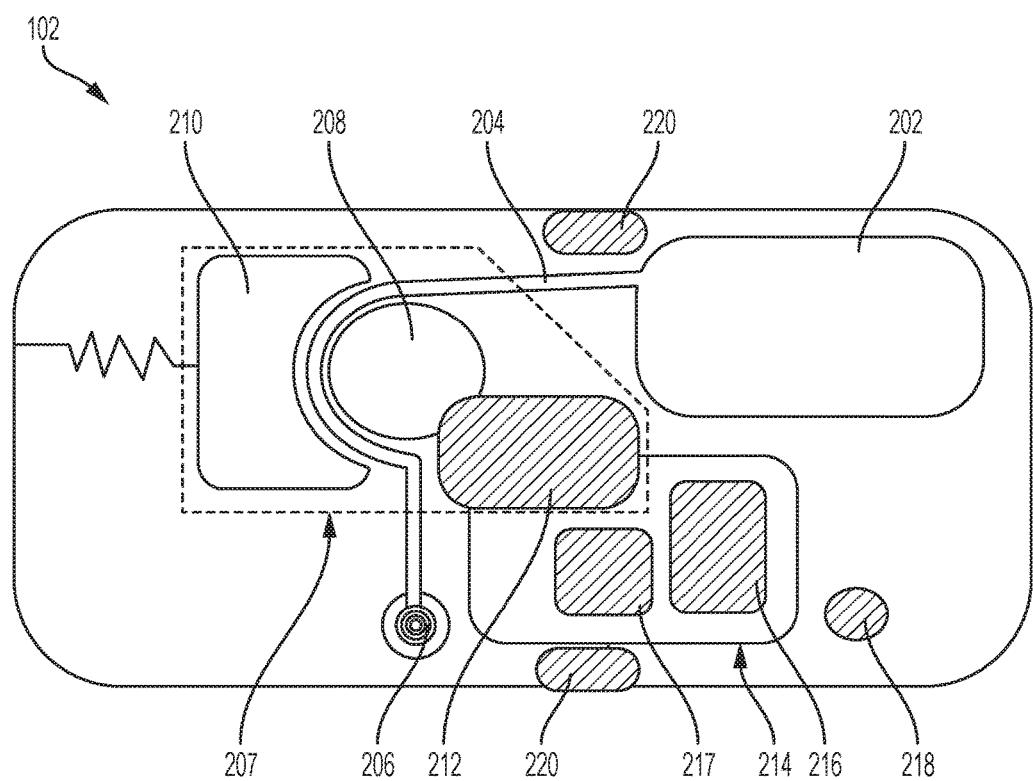
FIG. 2A and FIG. 2B are box diagrams showing a single-part dispensing unit (2A) and a two-part dispensing unit (2B) employing a peristaltic pumping mechanism.
Figure 2B:
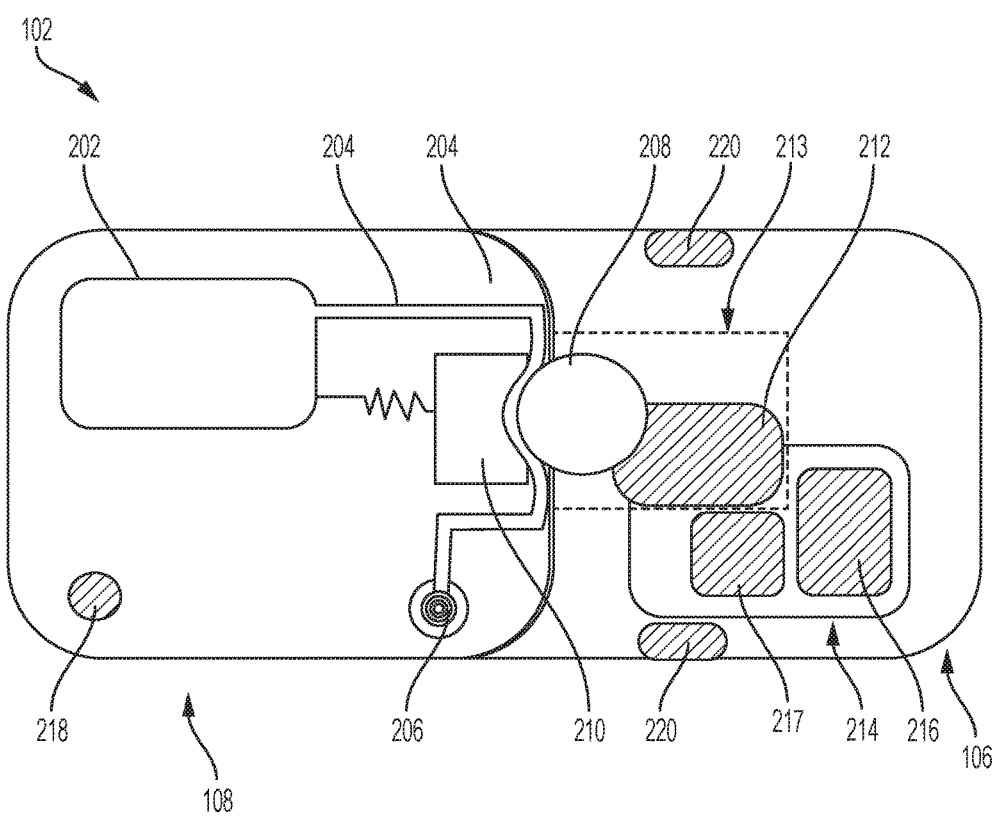

FIG. 2A and FIG. 2B show more detailed diagrams of dispensing units 102 employing a peristaltic pump 207 for dispensing the fluid to a user's body. FIG. 2A shows a single-part dispensing unit 102. The fluid is delivered from a reservoir 202 provided in the dispensing unit 102 through a delivery tube 204 to an exit port 206. The peristaltic pump 207 in FIG. 2A includes a rotary wheel 208 provided with rollers (not shown) and a stator 210. Rotation of the wheel 208 and pressing of the rollers against the stator 210 periodically positively displaces fluid within the delivery tube 204 by virtue of a peristaltic motion.

An example of such a positive displacement pump is disclosed in co-pending U.S. patent application Ser. No. 11/397,115. A driving mechanism 212 including a gear and a motor, such as for example a stepper motor, a DC motor, SMA actuator or the like, can be used to rotate the rotary wheel 208. The driving mechanism 212 can be controlled by electronic components 214 residing in the dispensing unit 102. These electronic components 214 can include a controller 216 that can be a microprocessor capable of executing control software such as is described below, a transceiver 217, and the like. An energy source 218, such as for example one or more batteries, a fuel cell, a photovoltaic cell or the like, can also be included in the dispensing unit 102 in FIG. 2A. Infusion programming of the dispensing unit 102 can be carried out by a remote control unit 104 capable of establishing a bidirectional communication link with the transceiver 217 provided in the dispensing unit 102. In an optional implementation, the infusion programming can also or alternatively be carried out via one or more manual buttons 220 provided on the patch unit 102.

FIG. 2B shows a two-part dispensing unit 102 that includes a reusable part 106 and a disposable part 108. The reusable part 106 includes a rotary wheel 208 and driving mechanism 212 that form part of a positive displacement pump mechanism 213, and electronic components 214 that can include a controller 216 that can be a microprocessor capable of executing control software such as is described below, a transceiver 217, and the like. The disposable part 108 of FIG. 2B includes a fluid reservoir 202, a delivery tube 204, an energy source 218, an exit port 206 and a stator 210. Pumping is possible after connecting the reusable part 106 with disposable part 108. This arrangement is described in our co-pending U.S. patent application Ser. No. 11/397,115. The power source 218, such as for example a battery, a fuel cell, a photovoltaic cell, or the like, can be included in the disposable part 108 as shown. Alternatively, the power source 218 can be included in the reusable part 106.

In some variations, the dispensing unit 102 can be configured to deliver more than one medicinal fluid. More than one disposable part 108, each including a reservoir 202 for a different fluid can then be included. Alternatively, a single disposable part 108 can include more than one reservoir. For delivery of multiple medicinal fluids from one device, the reusable part 106 can include more than one pumping mechanism 213, or alternatively a single pumping mechanism 213 can sequentially deliver each medicinal fluid or can draw medicinal fluids from more than one reservoir 202 simultaneously. Additional tubing, valves, or the like can be included as necessary to implement such a multiple fluid delivery system.

Figure 3A:
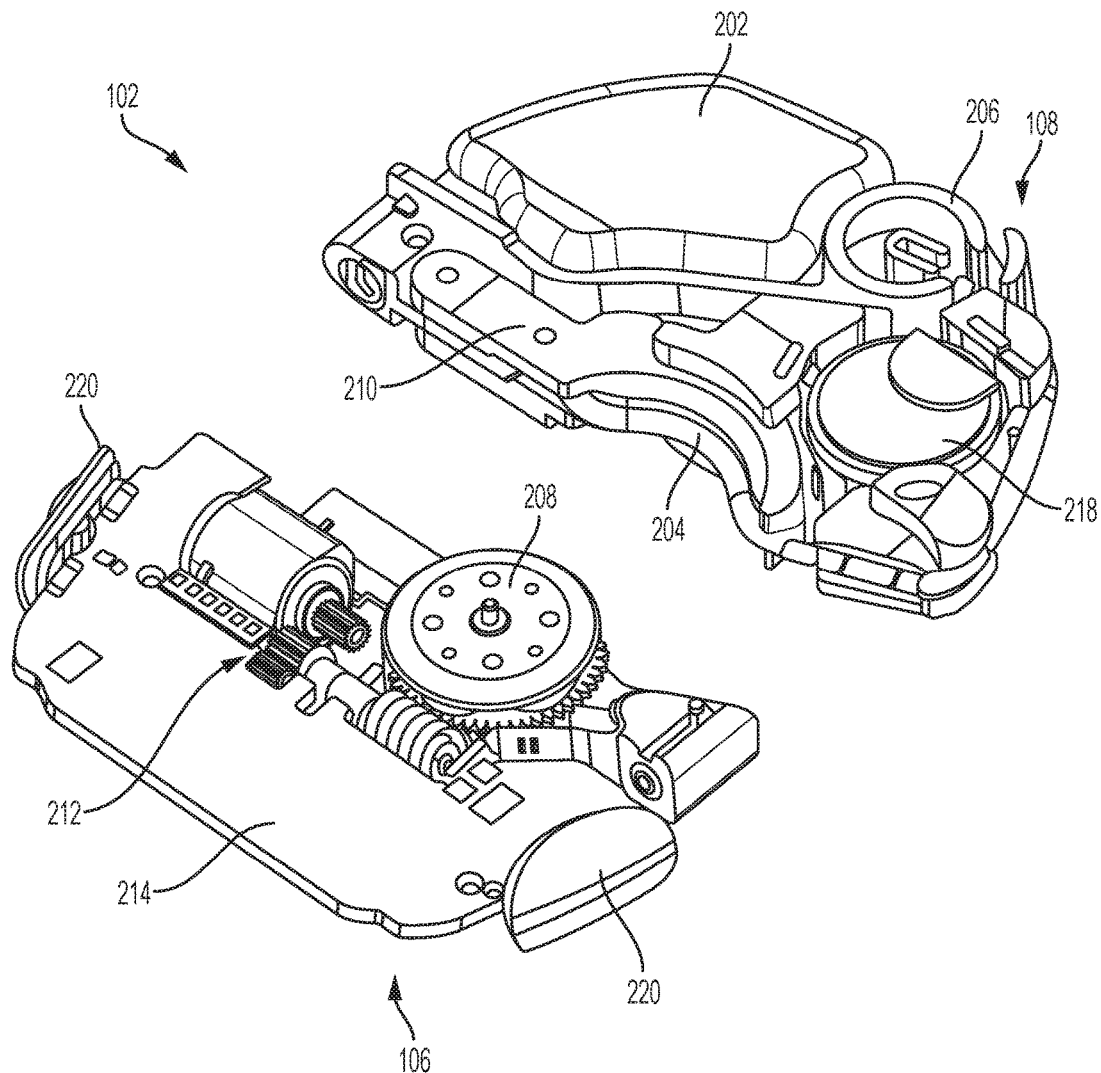
FIG. 3A and FIG. 3B are schematic diagrams showing an example of a two part dispensing unit employing a peristaltic pumping mechanism.
Figure 3B:
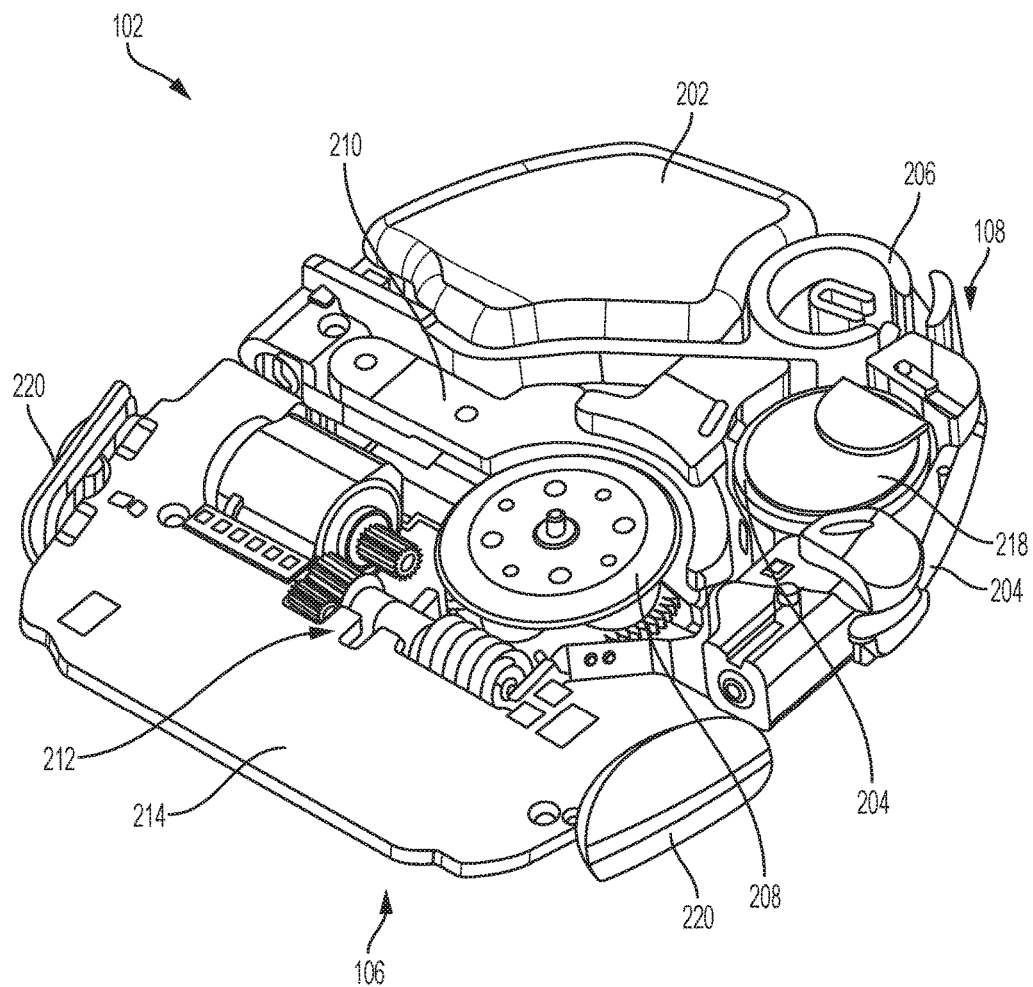

FIG. 3A and FIG. 3B are schematic diagrams showing an implementation of a two-part dispensing unit 102. FIG. 3A shows the two parts in detail. The reusable part 106 includes a positive displacement pump provided with a rotary wheel 208, a driving mechanism 212 and electronic components 214 on a circuit board. The disposable part 108 includes a reservoir 202, a delivery tube 204, an energy source 218, an exit port 206, and a stator 210. FIG. 3B shows the reusable part 106 and the disposable part 108 connected and ready for operation. In optional variations, the pumping mechanism can be of syringe-type, piezoelectric or the like.

Figure 4A:
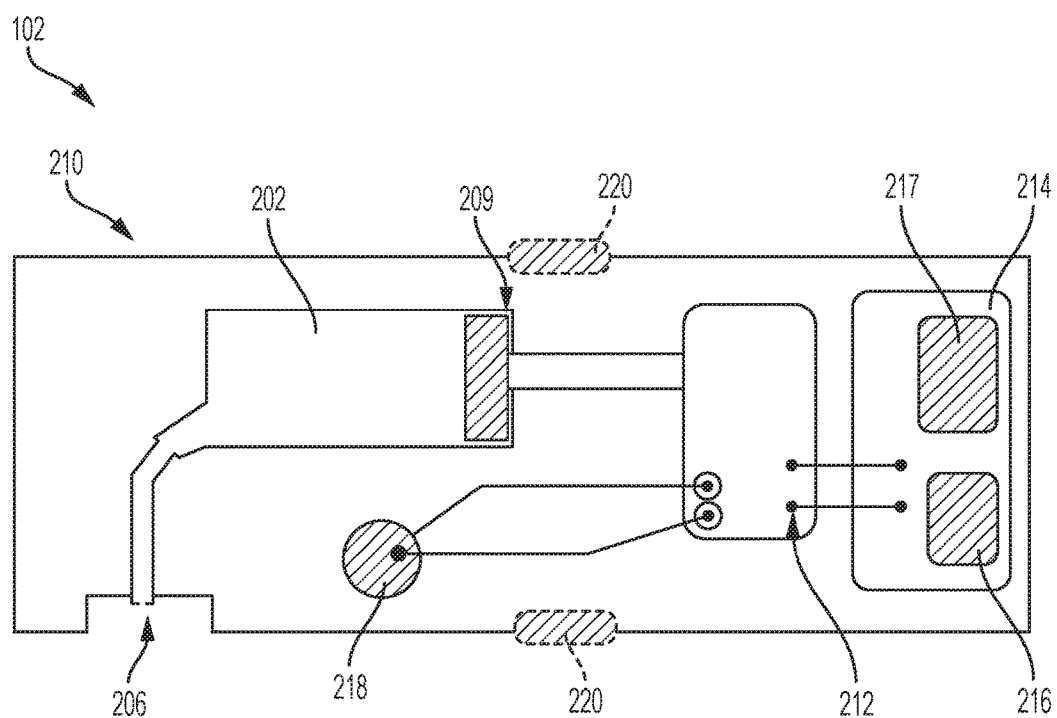
FIG. 4A and FIG. 4B are box diagrams showing a single-part dispensing unit (4A) and a two-part dispensing unit (4B) employing a syringe-piston pumping mechanism.
Figure 4B:
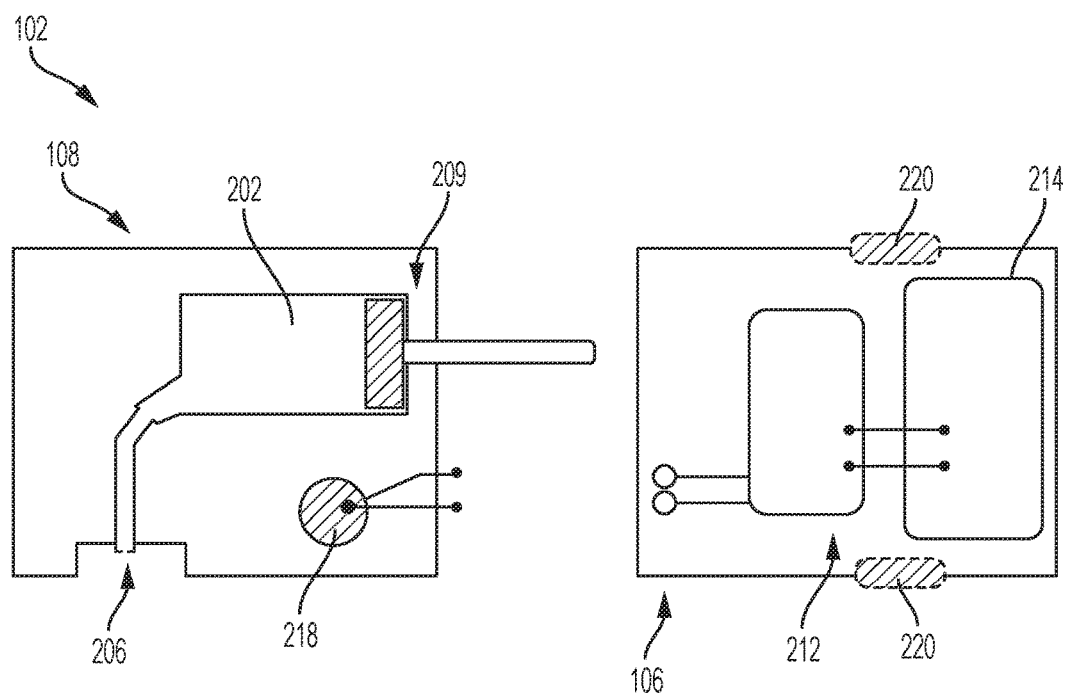

FIG. 4A and FIG. 4B show an implementation of the dispensing unit 102 employing a syringe pump for dispensing fluid to a user's body. FIG. 4A shows a single-part dispensing unit 102. The fluid is delivered from a reservoir 202 to the exit port 206. The reservoir 202 is provided with a plunger 209, which urges the fluid towards the exit port 206. A driving mechanism 212 is provided, which can include a motor, such as for example a stepper motor, DC motor, SMA actuator or the like, and a driving gear for driving the plunger 209. The driving mechanism 212 is controlled by electronics 214 which can include a controller 216, such as a microprocessor, and a transceiver 217. An energy source 218 is also provided such as is described above. Infusion programming can be carried out by a remote control unit 104 and/or by one or more buttons 220 optionally provided on the dispensing unit 102.

FIG. 4B shows a two-part dispensing unit 102 that includes a reusable part 106 and a disposable part 108 employing a pumping mechanism, which is a positive displacement pump. The reusable part 108 comprises driving mechanism 212, such as for example a motor and gear, electronic components 214, and at least one button 220. The disposable part 108 includes a reservoir 202 provided with plunger 209, energy supply means 218, and exit port 206. In optional variations, the plunger 209 can be located in the reusable part 106 or in the disposable part 108. If the plunger 209 is included in the disposable part 108, it can be configured to mate with the driving mechanism 212 on the reusable part 106. Infusion programming can optionally be carried out by a remote control unit 104 and/or by one or more buttons 220 optionally provided on the reusable part 106. Fluid dispensing is possible upon connecting the reusable part 106 with disposable part 108.

The two parts of the dispensing unit 102 described above can have finite serviceable lifetimes. The disposable part 108 can have a finite serviceable lifetime, which can be dictated by the size of its fluid reservoir 202, the capacity of the power source 218 and/or other factors. In some implementations, the disposable part 108 can be replaced once per one to three days. Longer or shorter service times for the disposable part 108 are also possible. Similarly, the reusable part 106 can also have a finite serviceable lifetime. Various mechanical or other moving parts, such as for example components of the pump mechanism 212, can wear out over time. The controller 216 can monitor the period of service for the reusable part 106 and can also optionally monitor one or more operational parameters for mechanical or other moving parts in the reusable part 106. If one or more operating parameters indicate a potential problem, an alert can be created to notify a user to replace the reusable part 106 sooner than otherwise scheduled. In some implementations, the reusable part 106 can be replaced approximately every three months. Longer or shorter service times for the reusable part 106 are also possible.

Control of the dispensing unit 102 can be accomplished by a user interface that can be manifested through input controls 220 on the dispensing unit 102. Such input controls 220 can optionally be positioned as shown in FIG. 2B, FIG. 3A, FIG. 3B, and FIG. 4B on the reusable part 106 or optionally on the disposable part 108. Control of the dispensing unit 102 can also be performed via wired or wireless communications with a remote control unit 104, a computer, or some other command means capable of relaying commands to the controller 216 on the reusable part 106. For wireless communication with a remote control unit 104 or other command means, the dispensing unit 102 can have an antenna or other wireless transceiver 217 that can be included either internally or externally on the reusable part 106.

Figure 5:
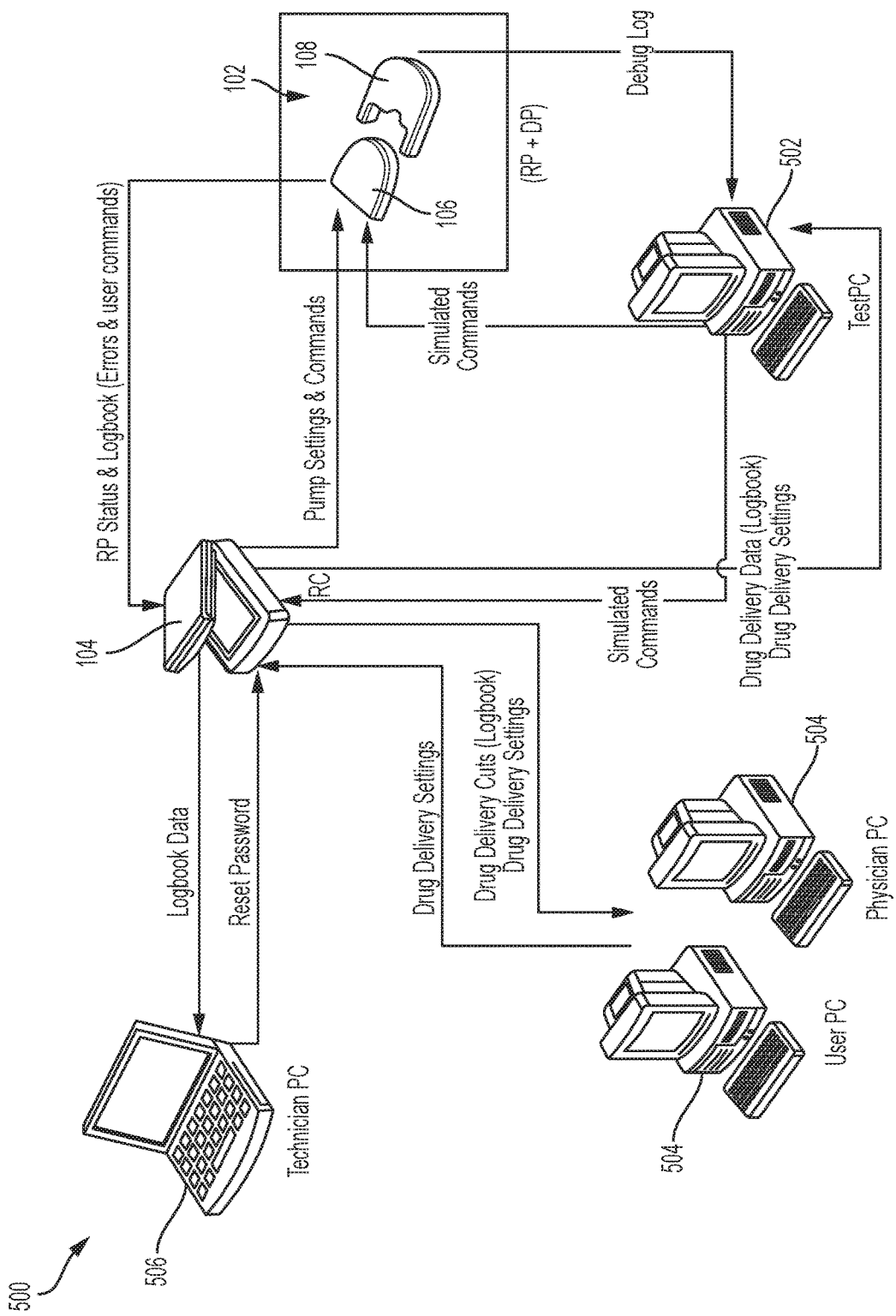
FIG. 5 is a relationship diagram showing possible control and communication elements of a medicinal fluid delivery device.

FIG. 5 is a relationship diagram 500 that illustrates various communication and control relationships of a medicinal fluid delivery device. As shown, a dispensing unit 102 that includes a reusable part 106 and a disposable part 108 can receive commands from a remote control unit 104, or in some variations from a test PC 502. The remote control unit 104 can provide commands related to dispensing unit 102 operation, and can receive the dispensing unit 102 status and logbook feedback as described in greater detail below. The test PC 502 can provide simulated commands to the dispensing unit 102 via a cable or a wireless communication link, and can receive debug data and logbook entries, from the dispensing unit 102. The test PC 502 and remote control unit 104 can communicate either wirelessly or via a cable to exchange simulated commands and/or to download logbook entries. The remote control unit 104 can also optionally communicate either via wired or wireless communication links with one or more other PCs 504 that can optionally include a user. PC and/or a physician PC, for example. Settings for dispensing unit 102 operation optionally including but not limited to medicinal fluid delivery settings can be sent to the remote control unit 104 and medicinal fluid delivery data (such as for example the logbook) and settings data can be transmitted to the PCs 502, 504. A technician PC 506 can also communicate with the remote control unit 104 via a wired or wireless link to exchange logbook data, settings information, to reset a password, and the like. One or more of a test PC, a user or physician PC 504, a technician PC 506, or a patient's computer or portable communication device operating specially adapted software can optionally perform one or more of the functions described here for the remote control unit 104. References to a remote control unit 104 herein are intended to cover these alternatives and other comparable devices, which are referred-to further by a general term command means.

In one implementation, methods are provided for pairing a dispensing unit 102 and a remote control unit 104. If a remote control unit 104 has not been paired to the dispensing unit 102 through some form of wired or wireless communication protocol, the dispensing unit 102 software can set its state to a waiting or pairing state, and then wait for a remote control communication pairing request from a remote control unit 104.

Figure 6:
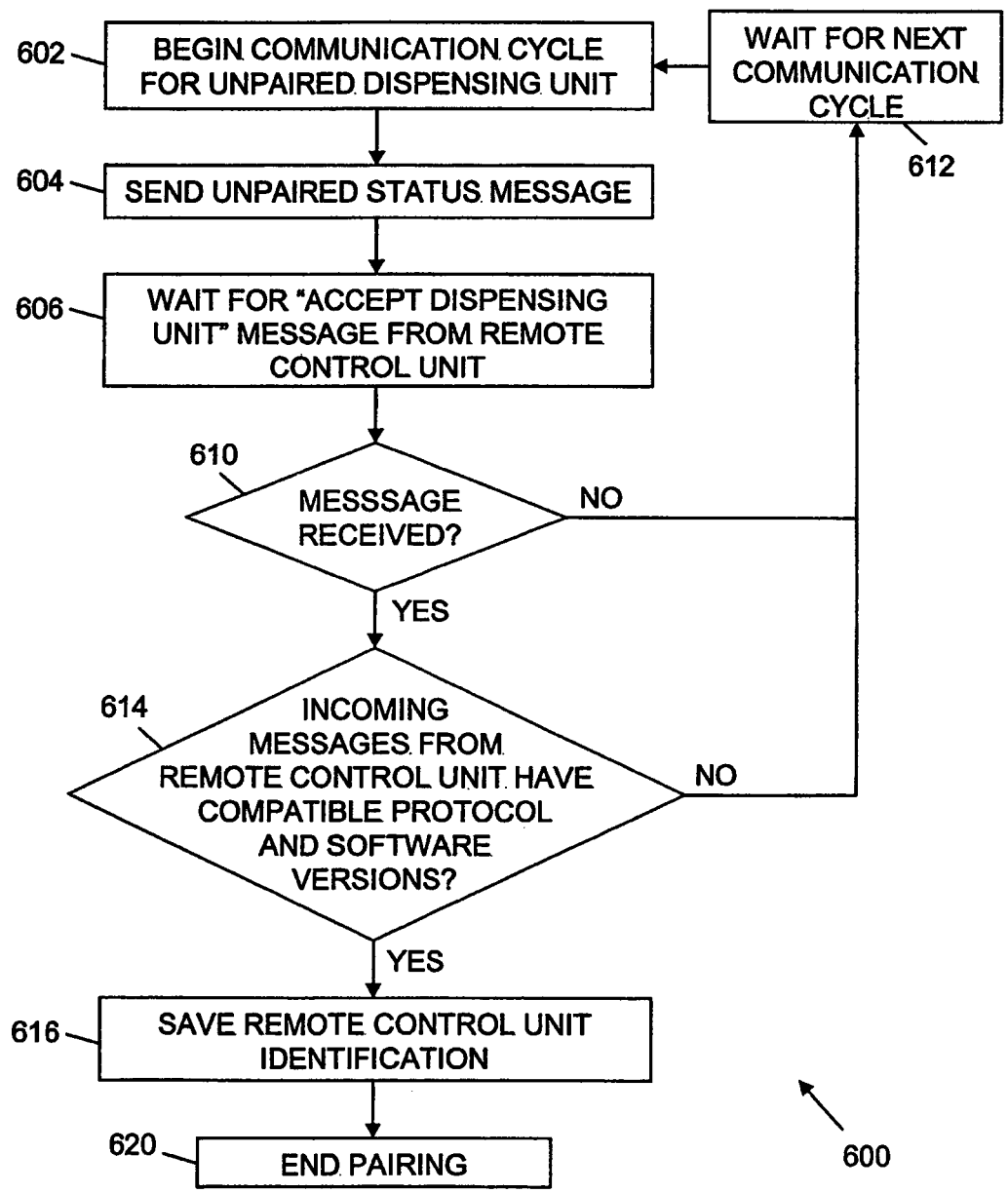
FIG. 6 is a process flow diagram illustrating a method for pairing a remote control unit with a dispensing unit on the dispensing unit side.

FIG. 6 is a process flow chart 600 illustrating an example of a pairing method between a dispensing unit 102 and a remote control unit 104 from the dispensing unit 102 side. At 602, a communication cycle begins for an unpaired dispensing unit 102. The controller 216 on the dispensing unit 102 can also optionally perform testing for software faults at this stage. At 604, the dispensing unit 102 sends an unpaired status message, optionally via its transmitter 217, and at 606 waits for a message from a remote control unit 104, such as for example an "accept dispensing unit" message, that indicates that the remote control unit 104 has received the unpaired status message sent at 604. At 610, the dispensing unit 102 controller 216 determines whether an "accept dispensing unit" message has been received. If no such message has been received, the dispensing unit 102 waits for the next communication cycle at 612 and then restarts the process at 602. When incoming messages from remote control units are received, the dispensing unit 102 determines whether the incoming messages have protocol and/or software versions that are compatible with those of the dispensing unit 102 at 610. The dispensing unit 102 software can also optionally verify the data integrity for data received from the remote control unit 104, such as for example by means of a cyclic redundancy check (CRC). If the protocol and software versions are not compatible, the dispensing unit 102 waits for the next communication cycle at 612 before beginning a new communication cycle at 602. If the protocol and software versions are compatible, an identification for the remote control unit 104 is saved by the dispensing unit 102 at 616. This completes the pairing process at 620. The dispensing unit 102 can send an acknowledgement message to the remote control unit 104 to confirm the pairing on the next communication cycle after the pairing has been completed.

Figure 7:
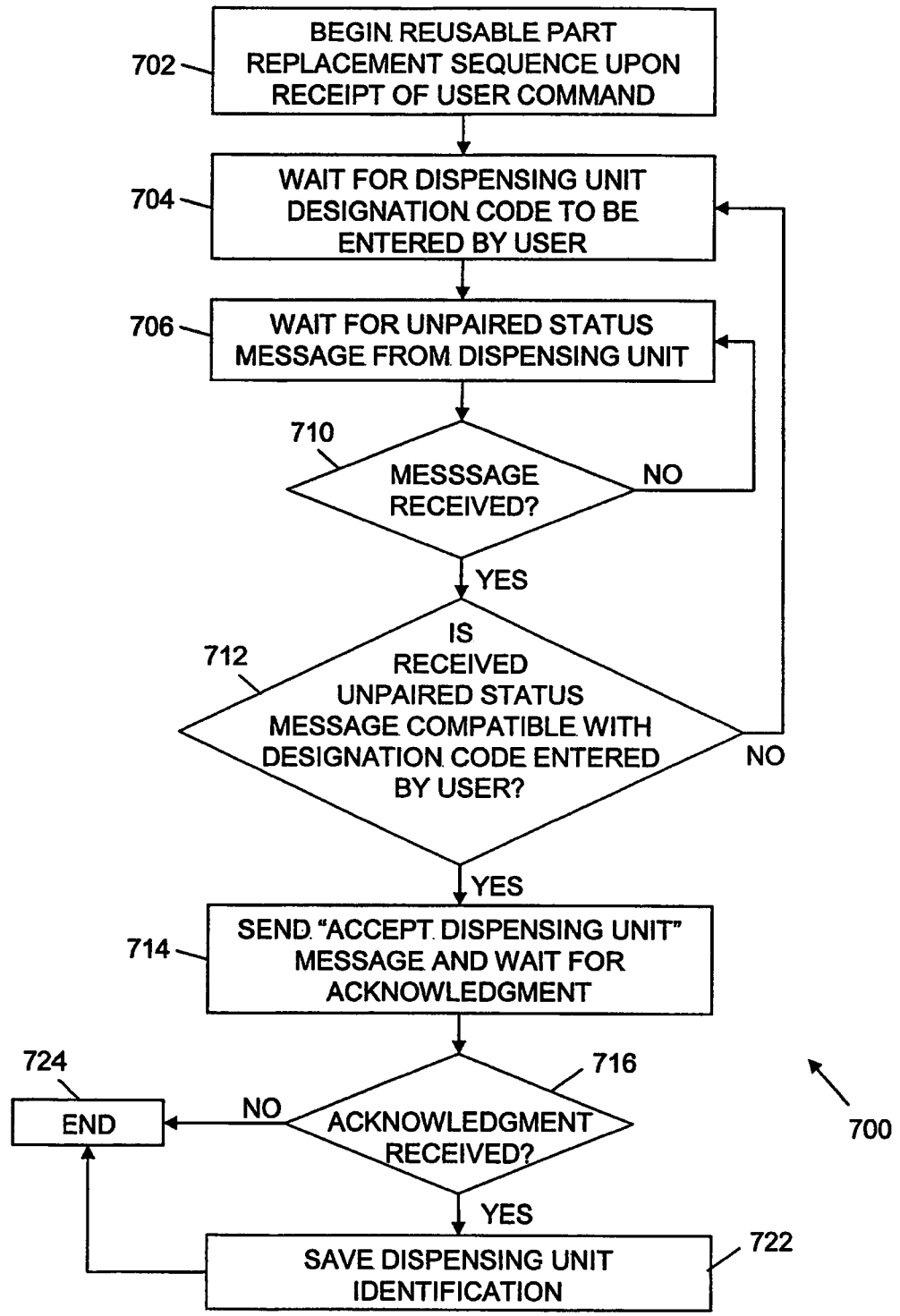
FIG. 7 is a process flow diagram illustrating a method for pairing a dispensing unit with a remote control unit on the remote control unit side.

FIG. 7 is a process flow chart 700 illustrating an example of a method for pairing a remote control unit 104 with a new dispensing unit 102 from the remote control unit 104 side. A dispensing unit 102 replacement sequence is started at 702 upon receipt of a command from a user, such as for example via a user interface on the remote control unit 104. The remote control unit 104 waits for a user to enter a designation code corresponding to a selected dispensing unit 102. The designation code can optionally be a complete serial number or other code that corresponds to a selected dispensing unit. Alternatively, the code entered by the user can optionally be a truncated version of a full designation code or a hash code that is convertable by one or more mathematical or lookup table functions to the full designation code. The remote control unit 104 then waits for receipt of an unpaired status message from the dispensing unit 102 at 706. A 710, if an unpaired status message has been received from the dispensing unit 102, the remote control unit 104 determines at 712 whether the message is compatible with the designation code entered by the user. If no such message is received at 710, the remote control unit 104 continues to wait for an unpaired status message from an unpaired dispensing unit 102 at 706. If the loop between stages 710 and 706 persists for longer than a threshold time, the remote control unit 102 can optionally end the pairing process. If the unpaired status message is compatible with the designation code entered by the user and is therefore available for pairing at 714 the remote control unit 104 sends an "accept dispensing unit" message or comparable notification to the dispensing unit 102. If the unpaired status message is not compatible with the designation code entered by the user at 712, the remote control unit returns to 704 to wait for a new dispensing unit 102 dispensing code to be entered by the user. If the waiting time persists for longer than a programmed threshold time, the process can optionally end. If the remote control unit 104 receives an acknowledgment to the "accept dispensing unit" message from the dispensing unit 102 at 716, the dispensing unit identification is saved at 722 and the process ends at 724. The programmed threshold waiting time can in one example be approximately as long as the duration of one or more communication cycles. If the pairing is not successful, for example if no acknowledgment is received from the dispensing unit 102, the process ends at 724 and should be repeated by the user.

A disposable part 108 replacement state can be entered when a disposable part 108 reservoir 202 is empty or when the disposable part 108 otherwise needs to be replaced. The control software can be configured to reject certain user commands during this state. The system can optionally limit the set of accepted commands during this state according to one or more predetermined command flow trees. Resumption of the drug delivery state can optionally be triggered by one or more specified steps or actions. The software can also be configured to disable or otherwise suspend drug delivery (either basal dosing or bolus administration) during this state and/or to reject input user commands to start or stop bolus injections, and/or reject messages from a non-paired remote control unit 104.

Figure 8:
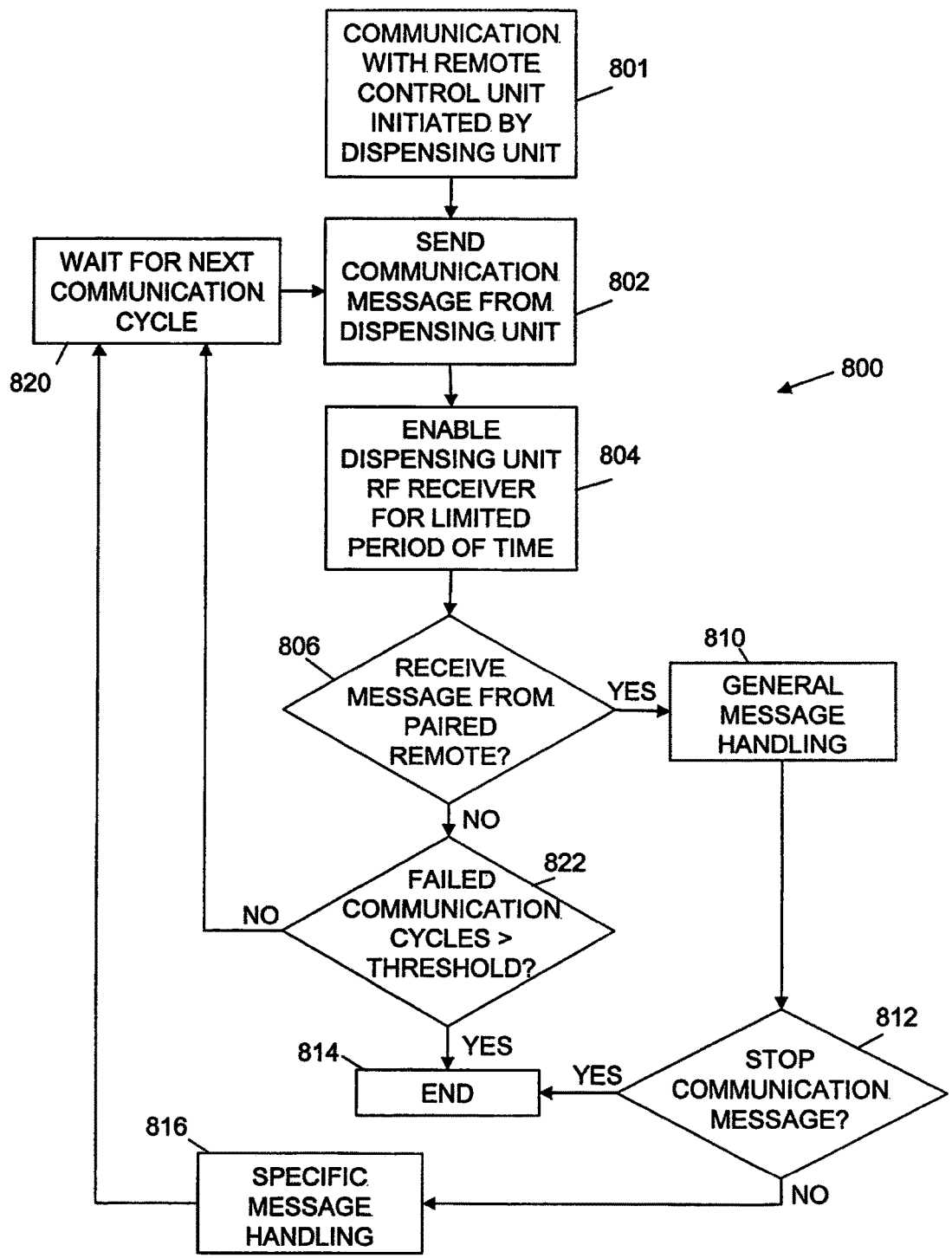
FIG. 8 is a process flow diagram illustrating a method for handling communications between a dispensing unit and a remote control unit on the dispensing unit side.

In another implementation, a method is provided for communication between a dispensing unit 102 and a remote control unit 104. FIG. 8 is a process flow chart 800 illustrating an example of such a method from the dispensing unit 102 side. In this example, communication between the dispensing unit 102 and the remote control unit 104 is initiated by the dispensing unit 102 at 801. The dispensing unit 102 sends a communication message at 802 and then enables a radio frequency or other wireless receiver on or in the dispensing unit 102 for a limited period of time at 804. Optionally, if the dispensing unit 102 is in wired contact with a remote control unit 104 or other command means, the communication message at 802 can also be sent via the wired connection.

If a message is received by the dispensing unit 102 from a paired remote control unit 104 at 806, the general handling of the incoming message is performed by the dispensing unit 102 controller 216 at 810. General message handling 810 can optionally include handling logbook entries such as is described below in regards to FIG. 10 and FIG. 11. Other general message handling aspects can optionally include time updates of remote control unit 104 and/or checking of software versions. During general message handling, the message from the paired remote control unit 104 is checked for whether it is a stop communication message at 812. If the message is a stop communication message, the communication process ends at 814. If the message is not a stop communication message at 812, the controller 216 on the dispensing unit 102 performs specific message handling at 816. This specific message handling can optionally include one or more of determining a pairing, suspend state, or drug delivery state, whether bolus commands have been given or basal profile programming changes made, or the like. After specific message handling, the dispensing unit waits for the next communication cycle at 820 before sending another communication message at 802.

If no message is received from a paired remote control unit 104 at 806, the dispensing unit 102 determines whether the number of communication cycles that have elapsed without a successful exchange of messages between the dispensing unit 102 and the remote control unit 104 has exceeded a programmed threshold at 822. If the threshold has been exceeded, the dispensing unit 102 suspends communication with the remote control unit 104 and ends the communication process at 814. If the threshold has not been exceeded at 822, the dispensing unit 102 waits for the next communication cycle at 820 before then sending a communication message at 802 on the next communication cycle.

Figure 9:
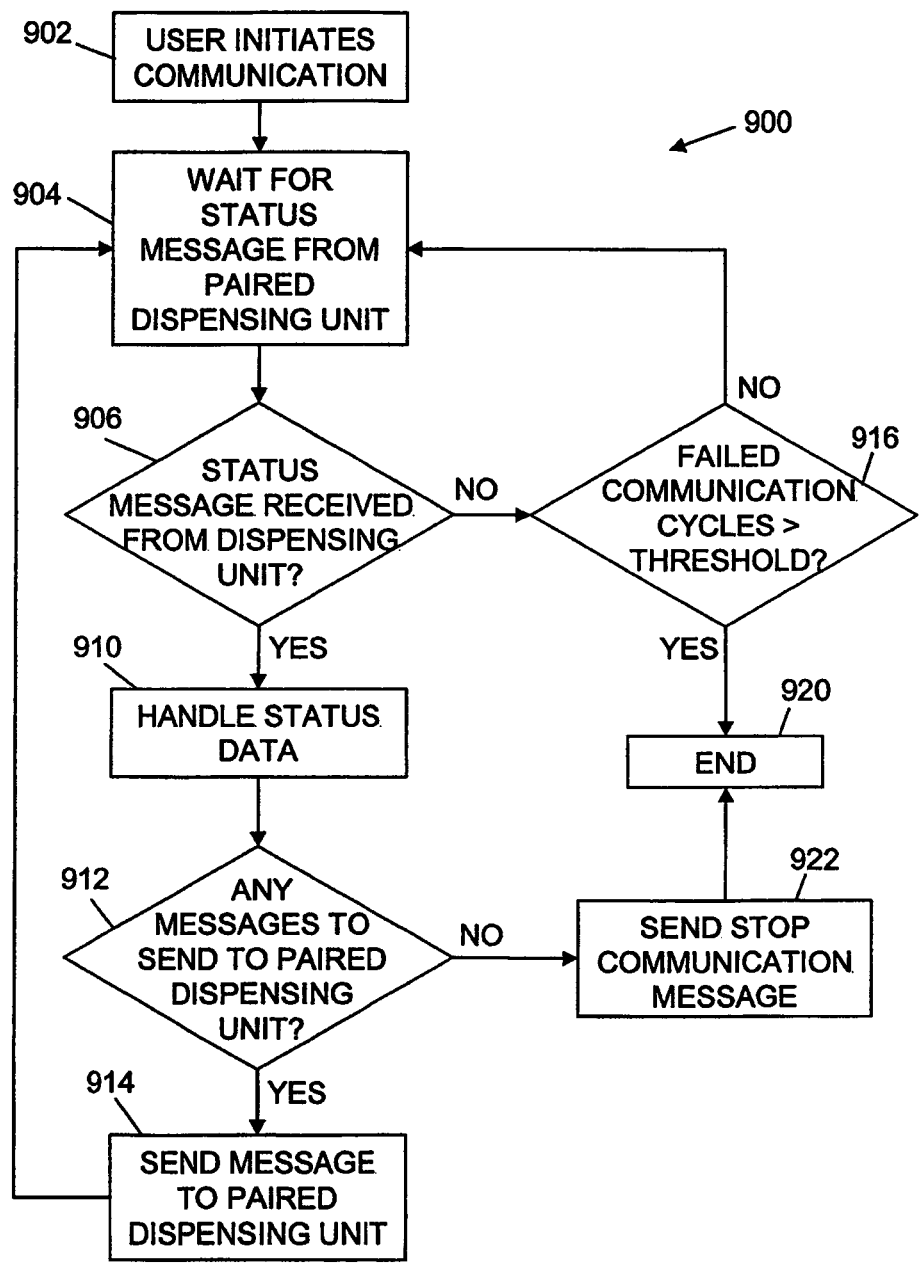
FIG. 9 is a process flow diagram illustrating a method for handling communications between a dispensing unit and a remote control unit on the remote control unit side.

FIG. 9 is a process flow chart 900 illustrating a method for communication between a dispensing unit 102 and a remote control unit 104 from the remote control unit 104 side. In this example, a user initiates communication at 902. Communication can optionally be initiated by pressing a switch on the remote control unit 104, by entering a start communication command via the remote control unit 104 user interface, in response to a timer that is set to initiate communication at some programmed or independently generated time interval, or the like. The remote control unit 104 waits for a status message from a dispensing unit 102 that is paired to the remote control unit 104 at 904. If a status message is received from the paired dispensing unit 102 at 906, the status data in the status message is handled by the remote control unit 104. This status message handling 910 can optionally include retrieving new dispensing unit 102 logbook entries received in the status message. If no acknowledgment is received with regard to the status message which was sent previously, the remote control unit 104 resends the previous message to the paired dispensing unit 102 at 914 and then waits for a status message from the paired device at 904. Alternatively, if the remote control unit 104 has unsent messages to send to the paired dispensing unit 102 at 912, the remote control unit 104 sends a message to the paired dispensing unit 102 at 914 and then waits for a status message from the paired device at 904. If no status message is received from a paired dispensing unit 102 at 906, the remote control unit 104 determines whether the number of failed communication cycles has exceeded a programmed threshold at 916. If the threshold has not been exceeded at 916, the remote control unit 104 returns to 904 to wait for a status message from the paired dispensing unit 102. If the number of failed communication cycles does exceed the threshold at 916, the communication sequences ends at 920. If the remote control unit 104 does not have any messages to send to the paired dispensing unit 102 at 912, the remote control unit 104 can send a stop communication message to the dispensing unit 102 at 922 and end the communication sequence at 920.

In another implementation, methods are provided for keeping and synchronizing logbook entries between a dispensing unit 102 and a remote control unit 104. The dispensing unit 102 controller 216 can maintain the system time and keep a timestamp within its logbook. The control software can also maintain, among other possible records, a disposable part 108 operation time record. This record can track elapsed time since the previous reusable part 106 startup event. The disposable part 108 time record can optionally include a logbook timestamp. In general the dispensing unit 102 logbook can includes items that are not yet known to the logbook maintained by the remote control unit 104. These items can include but are not limited to information regarding malfunctions of various parts of the dispensing unit, either on the reusable part 106 or the disposable part 108, and manual scheduling or termination of event such as boluses that are not commanded via the remote control unit 104 user interface. The software can further optionally maintain records of dispensing unit 102 operation hours (or other measure of operation time), disposable part battery voltage (or other measures of remaining power supply 218 capacity), disposable part 108 reservoir 202 level, and the hie in the flash memory. For each dispensing unit 102 operation time change, if the reusable part 106 is paired within a drug delivery or drug delivery suspend state, the software can increment a reusable part 106 operation time elapsed counter and update the battery or power supply 218 voltage and reservoir 202 level records. During basal drug delivery calculations; the software can use the relative system time in conjunction with the timestamp for locating the basal profile entry and temporary basal entry that correspond to the current system time. If a disposable part 108 is attached to a reusable part 106 for too many hours the software can set a reusable part 106 error.

Figure 10:
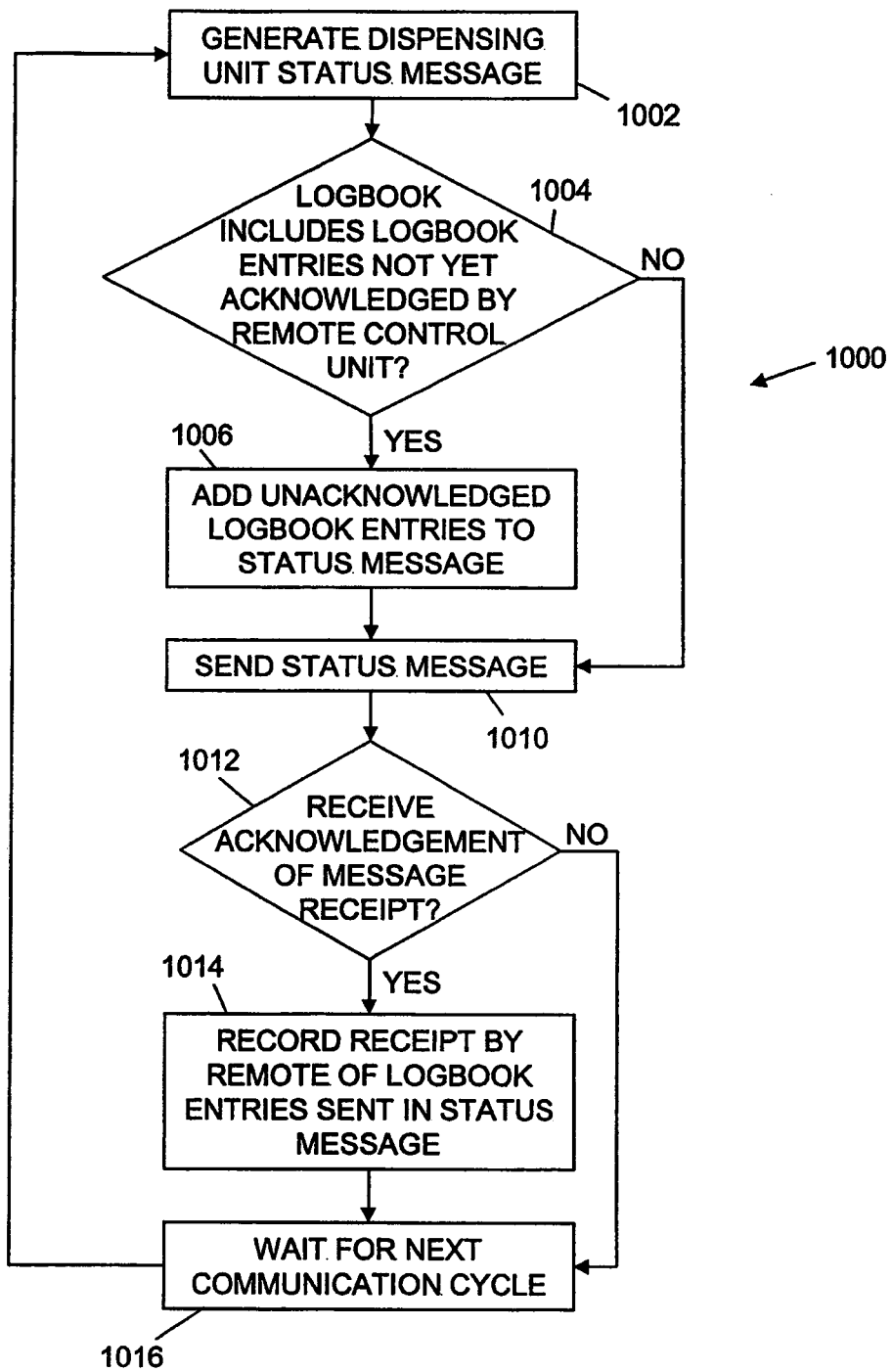
FIG. 10 is a process flow diagram illustrating a method for generating and propagating device status and logbook entry synchronization between a dispensing unit and a remote control unit on the dispensing unit side.

FIG. 10 is a process flow chart 1000 illustrating an example of a method for synchronizing logbook data between the dispensing unit 102 and its paired remote control unit 104 from the dispensing unit 102 side. The dispensing unit 102 generates a dispensing unit 102 status message at 1002. The status message can optionally include one or more of current status information of the dispensing unit 102 reservoir 202 level, power supply 218 voltage, and state (pairing, suspend, error, etc.); an acknowledgment of previously received messages from the remote control unit 104; and logbook data. On the dispensing unit 102 side, logbook data information is transmitted to the remote control unit 104 only if it is information that the remote control unit 104 has not yet received and acknowledged.

The dispensing unit 102 determines at 1004 whether the dispensing unit logbook includes logbook entries that have not yet been acknowledged as having been received by the remote control unit 104 that is paired to the dispensing unit 102. If unacknowledged logbook entries are included in the dispensing unit 102 logbook, they can be added to the status message at 1006. Logbook entries are transmitted to the remote control unit 104 from the dispensing unit 102 whenever there is sufficient space in a status message. Status messages can optionally be limited in size to streamline communication between the dispensing unit 102 and the remote control unit 104. Additional information that will not fit into the current status message can be held in a memory buffer on the dispensing unit 102 until it can be transmitted to the remote control unit 104.

If there are no unacknowledged logbook entries, the status message is sent without adding logbook information at 1010. If an acknowledgment of status message receipt is received from a paired remote control unit 104 at 1012, the receipt of the logbook entries sent in the last status message is recorded by the dispensing unit 102 at 1014. The dispensing unit 102 then waits for the next communication cycle at 1016 before generating a new status message at 1002.

Figure 11:
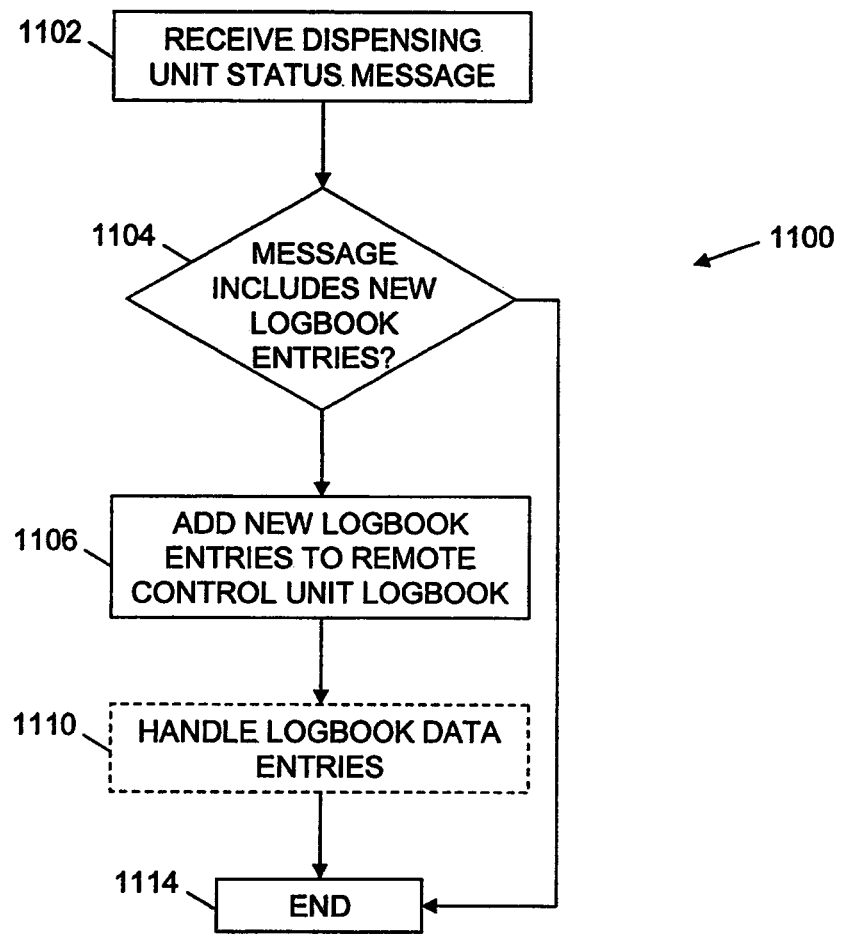
FIG. 11 is a process flow diagram illustrating a method for receiving dispensing unit status and extracting logbook data from it on the remote control unit side.

FIG. 11 is a process flow chart 1100 illustrating a method for synchronizing logbook entries between a remote control unit 104 and a dispensing unit 102 from the remote control unit 104 side. At 1102 the remote control unit 104 receives a dispensing unit 102 status message sent from the paired dispensing unit 102 at 1010 in FIG. 10. The remote control unit 104 determines whether the received message includes new logbook entries at 1104. If it does, the new logbook entries are added to the remote control unit 104 logbook at 1106. The remote control unit 104 optionally handles the logbook data entries at 1110 which can include sending an acknowledgment message to the paired dispensing unit 102 to confirm that the logbook entries transmitted in the most recent device status message have been received by the remote control unit 104 so that the device does not need to transmit these entries to the remote control unit 104 again. This process provides, among other benefits, the ability to minimize the communication bandwidth between the dispensing unit 102 and the paired remote control unit 104. Handling of logbook data entries at 1110 can also optionally include notifying the user if the status message includes an error alert. The logbook synchronization process ends at 1114 either after message handling as described, or if no new logbook entries are included in the status message.

Optionally, when a communication cycle with a paired remote control unit 104 ends, the local logbook on the dispensing unit 102 can be cleared. For example, if all of the logbook entries were sent to the remote control unit 104 and acknowledgement received at 1012, and if there are no errors in the logbook and the number of logbook entries is above some threshold that has been programmed to trigger an automatic clearing of the logbook, the device logbook can be cleared.

In various implementations, handling of errors identified by the control software and/or adding of logbook entries can be addressed using one or more features of the control software. Upon detecting an error in either the reusable part 106 or the disposable part 108 of the dispensing unit 102, the control software can add a logbook entry containing the error/alarm event and the time that it occurred. The time can optionally be either absolute time or time elapsed since some milestone event such as the most recent reusable part 106 startup. If the logbook is nearing full capacity, for example if storage remains available for only a limited number of additional entries, the software can set a flag or other indicator of this condition to warn a user. If an error is detected, the software can set an error flag or set a state indicator to, communicate information about the error to a user.

The control software can optionally be started or restarted upon replacement of a disposable part 108 in the dispensing unit 102. During this restart state, the software can disable drug delivery via the pump mechanism or other delivery mechanism in the same manner as if drug delivery were suspended for another reason, such as for example detection of an error or other fault. Communication with the remote control unit 104 or other command means such as a test PC 502, user or physician PC 504, a technician PC 506, or the like can also be suspended temporarily during this state. The software can also temporarily reject user commands that are entered via manual buttons 220 on the dispensing unit 102. In one implementation, if an identification code, such as for example a serial number, for the disposable part 108 does not match those required for the reusable part 106, an error flag can be set and/or a user can be notified using auditory, visual, or other notifications, optionally via error indicators or via the user interface on the dispensing unit 102, remote control unit 104, or other command means.

The control software can optionally run built in test routines to perform periodic integrity tests, and can add logbook entries, flags, or other notifications as necessitated by the test outcomes in addition to addressing any failures detected by the test routines. The control software can also search for errors in the logbook. If an error is detected either by the test routines or by a watchdog routine that periodically or continuously monitors one or more operational aspects of the dispensing unit 102, the control software can set an auditory, visual, or other indication to the user and also optionally change the dispensing unit 102 state to an error state. The error state can optionally indicate whether the error is in the reusable part 106 or the disposable part 108 or can even identify an individual component that has triggered the error. The control software can also monitor the operational time of the dispensing unit 102 as a whole or alternatively of the reusable part 106 or the currently in-use disposable part 108. If the operational time exceeds a maximum operational lifetime parameter that can be predefined, the software can set an error, a flag, or otherwise provide a notification to a user that maintenance or installation of a replacement part may be necessary. Upon an unexpected reset, the software can add an unexpected reset logbook entry and/or set an error indication or a flag to notify a user. If an expected reset occurs, such as for example at system start-up, the software can set a system startup feedback that can be auditory, visual, or other.

Medicinal fluid delivery rates can optionally be controlled using a basal delivery profile and one or more control routines for administering a bolus of additional medicinal fluid. A basal profile can be input by a user via the remote control unit 104 or other external control device, such as for example a test PC 502, user or physician PC 504, technician PC 506, or the like, over a wired or wireless connection to the medicinal fluid delivery dispensing unit 102. If a basal profile has not yet been initialized, the control software on the dispensing unit 102 can wait for one or more inputs to indicate a profile to use. These inputs can come from the remote control unit 104 or other command means, via a wired or wired less connection from a test computer or other control device, or the like. Optionally, the control software can receive a message from the remote control unit 104 requesting that a temporary profile be set. In response to this message, the control software can set a temporary basal delivery rate of the medicinal fluid to the patient. If one or more fluid delivery related parameters such as for example the programmed increment of a manually administered bolus, the maximum bolus size for a single manual injection, the maximum daily bolus, and/or the maximum daily basal dosing of the medicinal fluid are not yet initialized, the software can be configured to wait for a message to be input from a user.

After initialization, fluid delivery operations can be commenced. Upon entering the fluid delivery state, fluid delivery can be executed periodically or continuously. The software can limit the amounts of the medicinal fluid delivered in a given period of time according to one or more parameters. The software can allow an increment or decrement in the amounts of the medicinal fluid delivered within a given time period so that bolus command fluid delivery rate changes take effect immediately and so that temporary basal and basal profile changes take effect within next time period. During fluid delivery, the software can set the dispensing unit 102 into low power mode whenever possible. The software can maintain the reservoir 202 level by reducing the corresponding amounts for each motor pulse packet sent to the pump mechanism 212. If the reservoir 202 is empty, the software can set an error. The software can detect fluid delivery errors including but not limited to motor errors and fluid delivery blockage errors.

As noted above, the software can enable dosing of a patient using one or more manual boluses. For safety, the software can track the number of manual bolus administration commands entered by a user within a given time or alternatively in total. If successive commands to administer manual boluses are detected that would generate a bolus amount that is above some threshold level that is determined to exceed a recommended treatment dose or a total dose in a given period of time, the software can ignore additional manual bolus commands or key presses and/or set an auditory, visual, or other feedback notification to the user. This manual bolus safety feature can also include a feature that accounts for improper entry of a manual bolus command. For example, successive presses of a manual bolus key within some lower limit of time may be ignored as potentially being due to an errant duplicate manual button 220 press by a user. Similarly, the control software may also be configured to reject a user request for an additional bolus if previous bolus is still active or if too soon after a previous bolus. A threshold time within which no more than a certain number of bolus administrations or alternatively no more than a total bolus amount may be delivered within a specified time (e.g. one day, one hour, etc.) can be preset. If a bolus command from a user exceeds one of these thresholds, it can be rejected and/or a feedback can be given. If a manual bolus command is accepted, the software can optionally add a manual bolus logbook entry, set a auditory indication to the user, save the command data, and/or set a user indicator that a manual bolus has been administered.

A stop bolus command can also optionally be entered. In response to this command, if such a command is supported within the current system state, the control software can do one or more of adding a logbook entry to indicate that a stop bolus command was received (this entry can contain the amount of bolus that was not yet delivered); setting an auditory, visual, or other indication to the user; and setting a flag to indicate that a stop bolus command was entered. If the stop bolus command is not supported within the current dispensing unit 102 state, the control software can ignore the key press and provide a feedback to the user.

If the dispensing unit 102 receives a remote control unit 104 fluid delivery suspend command, it can suspend all fluid delivery, both bolus and basal. During this state the software can be programmed to reject user certain commands entered via the dispensing unit 102 or remote control unit 104, including but not limited to stop and start bolus injection commands. During this state the software can disable any fluid delivery. Upon receiving a fluid delivery resume or a start bolus injection message from a paired remote control unit 104, the software can change the device state to the fluid delivery state and resume fluid delivery immediately. Upon receiving a user entered bolus command, from the remote control unit 104, the software can change to the fluid delivery state and resume fluid delivery.

Upon receiving a set profile message from the remote control unit 104, the control software can perform a basal profile initialization and accordingly reject or accept the received command and add a logbook entry indicating receipt of a basal profile change message. The control software can reject the set profile message if the total amounts in the profile exceed a programmed maximum daily basal amount. Upon receiving a temporary basal message from the remote control unit 104, the software can perform a temporary basal profile initialization and accordingly reject or accept the command and add an appropriate logbook entry. The control software can reject a set temporary profile message from a remote control unit 104 if the total amounts in the profile are above the programmed maximum daily basal delivery amounts.

Implementations of the presently disclosed subject matter can optionally include one or more safety features. For example, the software can be programmed to detect and discard illegal operator commands and/or to ignore messages from any other remote control unit 104 besides a remote control unit 104 that has been specifically paired with the dispensing unit 102. The software can also optionally handle all software errors in an exception handler. The software can also detect errors using continuous tests throughout the operation period. The software can also continuously check the battery or power supply 218 level. If a battery level is below a minimum level, the software can set an error. Upon detection of an error or a state in which the software is not fully and properly initialized, the software can be configured to disable or otherwise suspend delivery of the medicinal fluid. The dispensing unit 102 software can reset itself by use of a watchdog timer interrupt. In some variations, the dispensing unit 102 software can clear the timer periodically at a pre-determined time interval to prevent an inadvertent software reset. After an unrecoverable error, the dispensing unit 102 can be locked out from drug delivery operations. During this state, the software can stop both of basal and bolus drug delivery, and reject certain remote control unit 104 messages. User commands entered via the manual buttons 220 can also be rejected. Periodic auditory, visual, or other indications can be provided to alert the user of the error state. In one variation, when a user presses a key combination that is not in accordance with a command recognition specification or that is otherwise not understood by the user interface, the software can ignore the key press and set an auditory, visual, or other feedback indication to the user. Errors that can be detected by the control software can include, but are not limited to, BIT errors occurring in either the reusable or the disposable parts of the dispensing unit 102, maximum operation time exceeded errors for either the reusable/disposable part alone or for an assembled device including a single disposable part/reservoir module, pump motor errors, software errors (e.g. logbook full, etc.), errors reported by a continuous test routine, watchdog errors, an empty fluid reservoir 202 error, low battery or power supply 218 errors, and blockage errors related to the fluid delivery path.

Power management features of the device as implemented by the software can optionally include one or more of prevention of simultaneous radio frequency wireless communications and motor operation, minimization of dispensing unit 102 power consumption by entering a low power mode whenever possible, and the like. Power conservation features can be implemented in one variation such that a user button press of one second is recognized by the software. Once a user button press is detected or upon communication initiation by a remote control unit 104, the software can cause the dispensing unit 102 to exits the sleep mode.

For each control software version, an additional basic software version can also optionally be provided. This test version can support additional wireless communication messages that may not be supported in the operational software and that thereby allow a dispensing unit 102 to be controlled and tested by a test PC 502 indirectly, using a remote control unit 104 as a mediator. The test software can include one or more features as discussed below. Upon receiving a user command simulation message from the remote control unit 104, the test software can simulate a manual button 220 press event on the dispensing unit 102. These events could include but are not limited to a manual bolus command or a stop bolus command. Upon receiving a clear pairing message from a remote control unit 104, the test software can clear the current remote control pairing and change the dispensing unit 102 state to pairing. Upon receiving a clear errors message from the remote control, the test software can clear all logbook errors and change the dispensing unit 102 state to a handle disposable part 108 replacement state. Upon receiving an error simulation messages from the remote control unit 104, the test software can generate corresponding events which can indirectly cause a dispensing unit 102 state change to an error state.

An additional cable controlled, hardware R&D test software version can also optionally be provided to allow the device hardware to be controlled directly through an RS232 or some other comparable physical cable connection. The cable controlled test software can support a specific set of hardware test communication messages, such as for example in full power operation mode. The hardware tests can allow a test PC to retrieve digital and A-to-D inputs and to generate system outputs.

In various implementations, the dispensing unit transceiver 217 can be an RF modem for example a Chipcon TBD-CC1110/CC2510 available from Texas Instruments of Dallas, Tex. and the dispensing unit processor can be the ARM7 provided by STMicroelectronics of Geneva, Switzerland. The software can be developed in a suitable programming language such as for example C or C++ or Assembler. Timer and sampling routines can use Assembler. The software can include one or more mechanisms for preventing variables from being corrupted due to simultaneous changes. The dispensing unit 102 as a whole and/or the reusable part 106 can be designed in one variation for static memory allocation.

Fluid delivery systems as described herein can optionally also include additional features, such as for example a capability to sense and/or monitor one or more metrics of patient health. In various implementations as described above, the dispensing unit can optionally also function as a sensing unit for sensing and monitoring concentration levels of analytes, such as for glucose in the ISF (interstitial fluid) or blood for example. Sensing can optionally be discrete, frequent or continuous. A dispensing unit 102 can optionally include both dispensing and sensing via one cannula that is placed subcutaneously. Then, the system can optionally function in various modes: closed loop, semi-closed loop or each apparatus (dispensing apparatus and/or sensing apparatus) independently. Information generated by such a sensing feature can be logged at the dispensing unit 102 and transmitted to a remote control unit 104 using one or more of the techniques and methods described above.

The subject matter described herein can be embodied in systems, apparatus, methods, and/or articles depending on the desired configuration. In particular, various implementations of the subject matter described herein can be realized in digital electronic circuitry, integrated circuitry, specially designed ASICs (application specific integrated circuits), computer hardware, firmware, software, and/or combinations thereof. These various implementations can optionally include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device.

These computer programs (also known as programs, software, software applications, applications, components, or code) can include machine instructions for a programmable processor, and can be implemented in a high-level procedural and/or object-oriented programming language, and/or in assembly/machine language. As used herein, the terms "machine-readable medium" and "computer-readable medium" refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a user, the subject matter described herein can optionally be implemented on a fluid delivery device including a computer, handheld communication device, single use remote control unit, or other command means as described herein having a display device, such as for example monitor like a CRT (cathode ray tube) or LCD (liquid crystal display, for displaying information to the user and optionally a keyboard and/or a pointing device, such as for example a keyboard, touch screen, track ball, or the like by which the user can provide input to the fluid delivery device. Other kinds of devices can optionally be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flow depicted in the accompanying figures and/or described herein do not require the particular order shown, or sequential order, to achieve desirable results. Other embodiments may be within the scope of the following claims.

What is claimed is:

1. A method for pairing a command means with a dispensing unit of a fluid delivery device, comprising:
   receiving a designation code entered at the command means by a user, the designation code identifying a specific dispensing unit;
   receiving an unpaired status message at the command means initiated by and sent from the dispensing unit and checking the unpaired status message to verify compatibility with the designation code entered at the command means by the user, the unpaired status message being the first message between the dispensing unit and the command means during the pairing of the command means with the dispensing unit;
   sending an accept dispensing unit message from the command means after verification of compatibility with the designation code entered by the user and waiting for an acknowledgment message from the dispensing unit; and
   saving identification information for the specific dispensing unit on the command means if the acknowledgment message is received.

2. The method of claim 1, further comprising testing for software faults on the dispensing unit before sending the unpaired status message.

3. The method of claim 1, further comprising waiting for a next communication cycle to resend the unpaired status message if no acceptance message is received from the command means.

4. The method of claim 1, wherein the command means comprises a remote control unit or a personal or laptop computer or handheld communication device.

5. The method of claim 1, further comprising receiving at the command means a user command to begin a reusable part replacement sequence.

6. The method of claim 1, further comprising establishing a one-to-one communication link between the command means and the specific dispensing unit.

7. The method of claim 1, further comprising ignoring messages received from other dispensing units to which the remote control unit is not paired.

8. The method of claim 1, wherein the command means prompts the user to enter a second designation code for another specific dispensing unit if compatibility between the specific dispensing unit and the command means cannot be verified.

9. The method of claim 1, wherein the command means ends the method if the unpaired status message is not received from the dispensing unit within a threshold time.

10. The method of claim 1, wherein the designation code comprises a hash code or other truncated representation of a full identification code for the dispensing unit.

11. A fluid delivery device comprising a fluid dispensing unit and a command means that is capable to execute software instructions that implement the method of claim 1.

12. The method of claim 1, wherein the designation code comprises a hash code or other truncated representation of a full identification code of the dispensing unit; the method further comprising converting the hash code or other truncated representation to the full identification code.

13. The method of claim 1, further comprising entering the dispensing unit in a replacement state and rejecting one or more user commands while in the replacement state.

14. A method for communicating between a dispensing unit of a fluid delivery device and a paired command means, comprising:
   initiating the pairing of the dispensing unit with the command means by:
      sending a communication message from the dispensing unit at a beginning of a current communication cycle;
      receiving a designation code entered at the command means by a user, the designation code identifying a specific dispensing unit;
      receiving an unpaired status message at the command means initiated by and sent from the dispensing unit and checking the unpaired status message to verify compatibility with the designation code entered at the command means by the user; and
      sending an accept dispensing unit message from the command means after verification of compatibility with the designation code entered by the user and waiting for an acknowledgment message from the dispensing unit;
   enabling, for a limited period of a time, a wireless receiver provided on the dispensing unit; handling an incoming message if the incoming message is received from the paired command means during the limited period of time; and
   waiting for a next communication cycle to send a next communication message from the dispensing unit.

15. The method of claim 14, wherein the command means comprises a remote control unit or a personal or laptop computer or handheld communication device.

16. The method of claim 14, further comprising suspending communication from the dispensing unit if the incoming message received from the paired command means is a stop communication message or if no message is received from the paired command means for greater than a threshold number of communication cycles.

17. The method of claim 14, further comprising sending a communication message from the dispensing unit on a next communication cycle after the current communication cycle ends.

18. A fluid delivery device comprising a dispensing unit comprising a controller that is capable to execute software instructions that implement the method of claim 14.

19. The method of claim 14, further comprising entering the dispensing unit in a replacement state and rejecting one or more user commands while in the replacement state.

* * * * *